(12) United States Patent
Driscoll

(10) Patent No.: US 12,020,787 B2
(45) Date of Patent: *Jun. 25, 2024

(54) TRIGGERED RESPONSES TO REAL-TIME ELECTROENCEPHALOGRAPHY

(71) Applicant: Data Vault Holdings, Inc., New York, NY (US)

(72) Inventor: Kerry Michael Albert Driscoll, Signal Hill, CA (US)

(73) Assignee: DATA VAULT HOLDINGS, INC., New York, NY (US)

( * ) Notice: Subject to any disclaimer, the term of this patent is extended or adjusted under 35 U.S.C. 154(b) by 548 days.

This patent is subject to a terminal disclaimer.

(21) Appl. No.: 17/011,036

(22) Filed: Sep. 3, 2020

(65) Prior Publication Data

US 2020/0402667 A1 Dec. 24, 2020

Related U.S. Application Data

(63) Continuation of application No. 15/145,340, filed on May 3, 2016, now Pat. No. 10,803,145.

(60) Provisional application No. 62/291,675, filed on Feb. 5, 2016.

(51) Int. Cl.
| | | |
|---|---|---|
| *G16H 10/60* | (2018.01) | |
| *G16H 40/63* | (2018.01) | |
| *G16H 50/20* | (2018.01) | |
| *H04L 67/1097* | (2022.01) | |

(52) U.S. Cl.
CPC ............ *G16H 10/60* (2018.01); *G16H 40/63* (2018.01); *G16H 50/20* (2018.01); *H04L 67/1097* (2013.01)

(58) Field of Classification Search
CPC ..... G16H 10/60; G16H 50/20; H04L 67/1097
See application file for complete search history.

(56) References Cited

U.S. PATENT DOCUMENTS

| | | |
|---|---|---|
| 4,291,255 A | 9/1981 | Alexeff |
| D281,576 S | 12/1985 | Akers |
| 5,083,571 A | 1/1992 | Prichep |
| 6,195,576 B1 | 2/2001 | John |
| 6,442,421 B1 * | 8/2002 | Le Van Quyen ...... A61B 5/372 128/920 |
| 6,735,467 B2 | 5/2004 | Wilson |
| 8,204,583 B2 | 6/2012 | Sackellares et al. |
| 8,954,135 B2 | 2/2015 | Yuen et al. |
| 9,000,927 B2 * | 4/2015 | Xiong ..................... G06F 21/32 340/5.82 |

(Continued)

*Primary Examiner* — Jay M. Patel
(74) *Attorney, Agent, or Firm* — Goodhue, Coleman & Owens, P.C.

(57) ABSTRACT

A method of processing EEG data. The EEG data for a user is read from a user utilizing one or more EEG input devices worn by the user. The EEG data is characterized utilizing one or more processing devices to generate characterized data. The characterized data is categorized utilizing the processing devices to determine a user activity and status of the user associated with the EEG data. The characterized data is analyzed to generate analyzed data. The characterized data is compared against controlled data for the user stored by the one or more processing devices. A service response is generated for one or more systems in communication with the one or more EEG devices to control one or more of ignition, locks, and operations of the one or more systems.

20 Claims, 4 Drawing Sheets

(56) References Cited

U.S. PATENT DOCUMENTS

| | | | |
|---|---|---|---|
| 9,042,971 B2 | 5/2015 | Brumback et al. | |
| 9,044,611 B2 | 6/2015 | Zhao et al. | |
| 9,049,998 B2 | 6/2015 | Brumback et al. | |
| 9,153,074 B2 | 10/2015 | Zhou et al. | |
| 9,712,587 B1* | 7/2017 | Alfishawi | A61B 5/165 |
| 2003/0195429 A1 | 10/2003 | Wilson | |
| 2004/0181162 A1 | 9/2004 | Wilson | |
| 2008/0167571 A1 | 7/2008 | Gevins | |
| 2008/0177197 A1* | 7/2008 | Lee | A61B 5/18 |
| | | | 600/545 |
| 2009/0124923 A1* | 5/2009 | Sackellares | A61B 5/7275 |
| | | | 600/544 |
| 2010/0016753 A1* | 1/2010 | Firlik | A61B 5/0006 |
| | | | 600/545 |
| 2010/0324440 A1 | 12/2010 | Moore et al. | |
| 2013/0211208 A1 | 8/2013 | Varadan et al. | |
| 2013/0241719 A1* | 9/2013 | Biswas | G06F 13/4022 |
| | | | 340/407.1 |
| 2013/0325924 A1 | 12/2013 | Moshfeghi | |
| 2013/0331660 A1 | 12/2013 | Al-Ali et al. | |
| 2013/0346168 A1 | 12/2013 | Zhou et al. | |
| 2014/0107493 A1 | 4/2014 | Yuen et al. | |
| 2014/0129935 A1 | 5/2014 | Nahon et al. | |
| 2014/0135631 A1 | 5/2014 | Brumback et al. | |
| 2014/0171819 A1 | 6/2014 | Patterson | |
| 2014/0223462 A1 | 8/2014 | Aimone et al. | |
| 2014/0275829 A1 | 9/2014 | Berezhnyy et al. | |
| 2014/0275835 A1 | 9/2014 | Lamego et al. | |
| 2014/0276188 A1* | 9/2014 | Jardin | A61B 5/7267 |
| | | | 600/544 |
| 2014/0277273 A1 | 9/2014 | Zhao et al. | |
| 2014/0316230 A1* | 10/2014 | Denison | A61B 5/168 |
| | | | 600/545 |
| 2014/0329537 A1 | 11/2014 | Huang | |
| 2015/0012111 A1 | 1/2015 | Contreras-Vidal et al. | |
| 2015/0112158 A1* | 4/2015 | He | A61B 5/746 |
| | | | 600/301 |
| 2015/0126845 A1 | 5/2015 | Jin et al. | |
| 2015/0126892 A1* | 5/2015 | Kim | A61B 5/372 |
| | | | 600/545 |
| 2015/0199010 A1* | 7/2015 | Coleman | H04L 67/01 |
| | | | 345/156 |
| 2015/0227702 A1* | 8/2015 | Krishna | A61B 5/7257 |
| | | | 705/2 |
| 2015/0246225 A1 | 9/2015 | Zhao et al. | |
| 2015/0256607 A1 | 9/2015 | Eom et al. | |
| 2015/0257674 A1 | 9/2015 | Jordan et al. | |
| 2015/0297109 A1 | 10/2015 | Garten et al. | |
| 2015/0313498 A1 | 11/2015 | Coleman et al. | |
| 2015/0332603 A1 | 11/2015 | Aravkin et al. | |
| 2016/0022167 A1* | 1/2016 | Simon | A61B 5/381 |
| | | | 600/301 |
| 2016/0061457 A1 | 3/2016 | Armstrong et al. | |
| 2017/0225677 A1* | 8/2017 | Yoshida | A61B 5/6893 |

* cited by examiner

TRIGGERED RESPONSES TO REAL-TIME ELECTROENCEPHALOGRAPHY

RELATED APPLICATIONS

This Application claims priority to U.S. provisional patent application Ser. No. 62/291,675 entitled "SECURE MOBILE COMPUTER NETWORK FOR CONTENT TARGETING AND TRIGGERED RESPONSES BASED ON REAL-TIME ELECTROENCEPHALOGRAPHY OR BINUARAL BEATS DATA", filed Feb. 5, 2016, and U.S. utility patent application Ser. No. 15/145,340 entitled "TRIGGERED RESPONSES BASED ON REAL-TIME ELECTROENCEPHALOGRAPHY" filed on May 3, 2016, the entire contents of which are hereby incorporated by reference in their entirety.

BACKGROUND

I. Field of the Disclosure

The illustrative embodiments relate to processing electroencephalography (EEG) signals in real-time. More specifically, but not exclusively, the illustrative embodiments relate to a system and method for processing brain wave data including EEG data in combination with at least a characterized and categorized information determined for a user.

II. Description of the Art

In recent years the development and commercialization of devices that capture noninvasive EEG data has made possible observing a person's brain activity. In some cases, these devices have multiple sensors or probes that are positioned on or within a person's skull, ears, or other positions on the head of the user. As a result, brain wave data may be effectively captured. Unfortunately, solutions for management, processing, and utilization of biometric brain wave data are very limited or non-existent. In particular, there is a lack of standardization that would enable the effective capturing, processing, and reporting of EEG data.

SUMMARY OF THE DISCLOSURE

One embodiment provides a method of processing EEG data. The EEG data for a user is read from a user utilizing one or more EEG input devices worn by the user. The one or more EEG input devices sense EEG data and biometrics of the user. The EEG data is characterized utilizing one or more processing devices to generate characterized data. The characterized data is categorized utilizing the processing devices to determine a user activity and status of the user associated with the EEG data. The characterized data is analyzed to generate analyzed data. The characterized data is compared against controlled data for the user stored by the one or more processing devices. A service response is generated for one or more systems in communication with the one or more EEG devices to control one or more of ignition, locks, and operations of the one or more systems. Another embodiment provides a processing system including a memory storing a set of instructions and a processor executing the set of instructions to perform the method described above.

Another embodiment provides a processing system for EEG data. The system includes input devices sensing EEG data from a number of users. The input devices are worn by the plurality of users and capture the EEG data from the plurality of users. The system includes a number of sensors that capture measurements including biometric data of the number of users, orientation, and speed of the number of users. The system includes a processor that characterizes the EEG data received from the plurality of users to generate characterized data, categorizes the characterized data utilizing the one or more processing devices to determine a user activity and status of each of the plurality of users associated with the EEG data, analyzes the characterized data to generate analyzed data, wherein the characterized data is compared against controlled data for the user stored by the one or more processing devices, and generates a service response for one or more systems in communication with the one or more EEG devices to control one or more of ignition, locks, and operations of the one or more systems in response to the generated data and the biometrics.

Another embodiment provides a system, device, and method of processing EEG data. The EEG data for a user is received at a server from one or more EEG input devices. The EEG data from the user is characterized utilizing the server to generate the characterized data. The characterized data is categorized utilizing the server. The characterized data is analyzed to generate analyzed data. The analysis includes at least comparing the analyzed data against control data. A service response is generated utilizing the server to process the analyzed data. Another embodiment provides a processing system including a memory storing a set of instructions and a processor executing the set of instructions to perform the method described above.

Another embodiment provides a processing system for EEG data. The processing system includes a number of input devices that receive EEG data from a plurality of users. The processing system further includes a characterization server that characterizes and categorize the EEG data received from the number of users to generate characterized data. The processing system further includes an analysis server that analyzes the characterized data by comparing the characterized data against control data to generate analyzed data. The processing system further includes a trigger server that generates a number of service response for each of the number of users in response to the analyzed data. The trigger server communicates the number of service responses to devices associated with each of the number of users or input devices.

BRIEF DESCRIPTION OF THE DRAWINGS

Illustrated embodiments of the present invention are described in detail below with reference to the attached drawing figures, which are incorporated by reference herein, and where.

DETAILED DESCRIPTION OF THE DISCLOSURE

Figure 1:
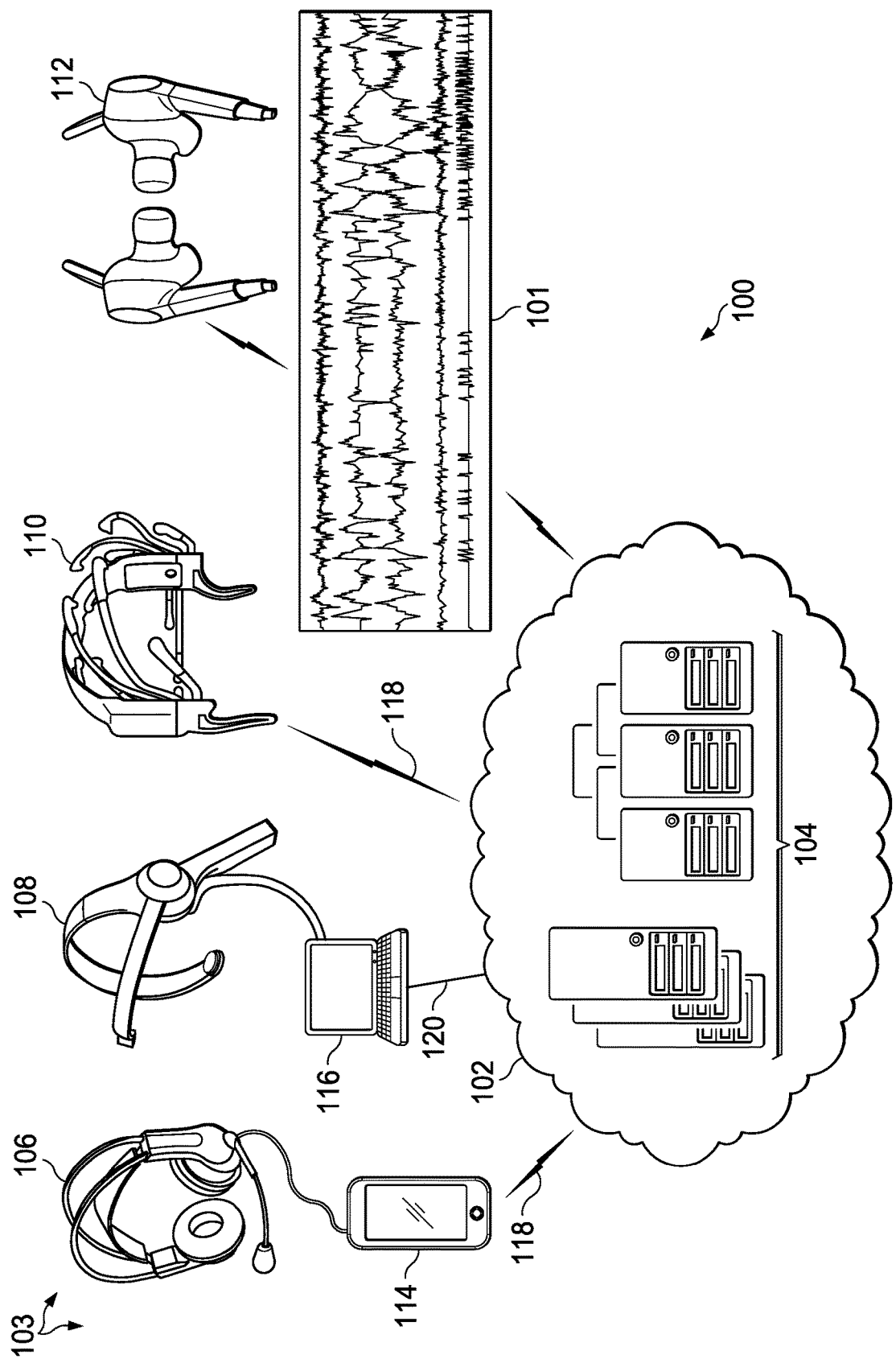
FIG. 1 is a pictorial representation of a processing system for EEG data in accordance with an illustrative embodiment.

The illustrative embodiments provide systems, devices, platforms, and methods for processing brain wave data including embodiments that use EEG data in combination with a user profile, mental state, characterizing information (e.g., age, sex, ethnicity, age, mental state, etc.), and categorization information. One embodiment provides for securely obtaining EEG brain wave data from any number of devices, systems, equipment, networks, components or peripherals. In one embodiment, the brain wave data may be characterized and categorized. For example, the brain wave data sets may then be systematically analyzed within a variety of specialized fields-of-use, such as video gaming, military, medical, and so forth. The analysis of the brain wave data sets may be securely performed utilizing through any number of networks (e.g., cellular, local area network (LAN), wide area network (WAN), Ethernet network, etc.) or native processing platforms. The processing system utilized to process and analyze the brain wave data may perform comparisons, normative analysis, and application specific service responses. The processing of the brain wave data may be performed automatically utilizing a single device (e.g., server, wireless device, personal computing device, etc.) or through a combination of systems and devices (e.g., cloud network, server farms, etc.).

The illustrative embodiments leverage the power of EEG reading devices and increases in mobile and networked processing power to more effectively analyze EEG data. As a result, the EEG data may be more effectively captured and utilized for numerous fields-of-use. For example, the EEG data may be processed and analyzed utilizing a standard format that may be adjusted or customized for any number of industries, fields-of-use, or groups of users. The illustrative processing platforms may utilize any number of cloud networks, mobile systems, database management, data portal interfaces, and acquiring technologies. Security standards, protocols, and signals, including encryption may be utilized to secure the EEG data before and after processing to protect user confidentiality, privacy, as well as legal rights, such as those provided by HIPAA. The illustrative embodiments provide systems and networks that are adapted to provide sufficient security and data transfer to enable it EEG data to be securely captured and processed.

The processed brain wave data is utilized to generate and assemble unique service responses or other actions. In one embodiment, the unique service responses may include 1) adaptive targeted content, 2) computer code, or 3) active trigger commands. The adaptive targeted content may include video, audio, html, digital images, mobile application content, video game content, 3D printing data, instructions, algorithms, and/or any other content that may be communicated or produced by a computer or wireless device. Computer code may include scripts, database data or instructions, home automation commands, computing, financial, or mathematical algorithms that include java, JavaScript, xml, html, and/or other programming languages. The active trigger commands may include instructions, commands, navigation, controls or signals used to activate, invoke, or control action of devices, machines, systems, equipment, components, digital environments, or physical environments. The service responses may be utilized to adjust stimuli, conditions, parameters, data, or information presented to the user or made to the environment of the user. As a result, the brain waves of the user as well as the associated EEG data may be adjusted in real-time to meet desired levels, thresholds, outputs, results, conditions, or effects.

The perception and processing of brain wave data may be performed for specific fields-of-use, categories, endeavors, systems, or facilities including, but not limited to, medical, human performance, military, construction, crisis management, correctional facilities, behavioral healthcare, scientific study, travel, security operations, and any number of other fields. The illustrative embodiments provide customizable data characterizations, modalities, and services responses that may be based on analysis of below average, normative, and exceptional brain wave data sets pertaining to each category or field-of-use. The illustrative embodiments may provision automated service responses that may help the user (e.g., perform necessary or desired tasks, relax, concentrate, etc.).

The illustrative embodiments provide for the effective management, processing, and utilization of brain wave data and production of systematic homogenous and usable standardization for the production of targeted digital data and content. The illustrative embodiments provide for the creation of real-world responses, triggers, and actionable data sets derived from the EEG data. Standardized and ubiquitous systems, methods, and devices for ingesting, processing, reporting, and acting on the EEG data may provide very valuable in numerous fields-of-use.

FIG. 1 is a pictorial representation of a processing system 100 for EEG data 101 in accordance with an illustrative embodiment. The processing system 100 may represent a platform, environment, or system for processing EEG data 101. The processing system 100 may include a network 102. In one embodiment, the network 102 may receive and process the EEG data 101 from the input devices 103.

The EEG data 101 may represent data captured by any of the input devices 103 for any number of users. The EEG data 101, represents the recorded electrical activity of a user's brain, such as voltage fluctuations resulting from ionic current within the neurons of the brain. The EEG data 101 from each of the input devices 103 will be distinct and unique as the users utilizing the input devices. For example, the patterns, frequencies, amplitudes, thresholds, and sensor readings for the EEG data 101 may vary significantly. The brain is made up of approximately 100 billion nerve cells. The activity of these neurons in the brain tissue creates active current sources that cause local electrical potential to fluctuate with a great deal of variability. As noted, each brain is unique both physically and functionally. The folding of the cortex of the human brain is highly individualized such that the characteristics of the external surface of the brain (as folded) affect the electrical potentials within the brain. The processing system 100 may be utilized to process the EEG data 101 as a way of treating diseases, processing the EEG data 101, and generating various stimuli. In one embodiment, a single user may wear or utilize a number of different input devices.

The network 102 may include network components 104. The network components 104 may represent any number of servers, databases, switches, routers, bridges, modems, mainframes, hardwired connections, wireless connections, private networks (e.g., fiber optic, Ethernet, LANs, etc.), public networks, or other devices, systems, equipment, or components. In one embodiment, the network 102 may represent a distinct processing platform for processing the EEG data 101 from the input devices 103. The EEG data 101 may be received in any number of formats. In one embodiment, the EEG data 101 is received as raw brain wave data that is processed within the network 102. In another embodiment, the EEG data 101 may be processed or minimally processed by the input devices 103. For example, the EEG data 101 may be packetized, digitized, or otherwise formatted for communication to the network 102 for processing and analysis.

In one embodiment, the input devices 103 may include input devices 106-112. The input devices 103 may represent any number of noninvasive or invasive devices. For example, the input devices 103 may include sensors, probes, pins, or electrodes that are positioned against, adjacent, or within the head, ear canal, or scalp of the user. The input devices 103 may be configured to both receive and generate signals for receiving the EEG data 101 as well as modifying, controlling, or enhancing the EEG data 101. For example, the input devices 103 may utilize optogenetics whereby neurons within the brain are controlled with light. Using optogenetics, a light-sensitive molecule may be inserted into the cell surface of a neuron. The light-sensitive molecule may then allow an outside user to trigger or inhibit the firing of the neuron by pulsing a specific frequency of light. Common noninvasive input devices 103 may include headsets, deep ear probes, graphing patch, sunglasses, wearables, helmets, hearables, electronic stickers, electronic headgear, or so forth.

The input devices 103 may also generate or communicate audio, video, optical, electrical, magnetic, or other signals, waves, media, communications, or stimuli that may be communicated directly or indirectly to the user (e.g., brain, ears, eyes, skin, etc.). As a result, the input devices 103 may represent EEG devices that may both read EEG data 101 as well as generate stimuli that affects or changes the EEG data 101. The input devices 103 may be utilized to shape the brain waves, response, mental status, physical status, or condition of associated users for health reasons, enhanced performance, experiments, or so forth.

In one embodiment, the input devices 103 may reliably capture the EEG data 101 without invasive probing or biological insertions that require the penetration of skin, brain tissue, ear canal, or other portion of the exterior of the skull. The input devices 103 may represent brain computer interfaces (BCI) that capture the EEG data 101 for recording, processing, utilization, or display to one or more users. The processed EEG data 101 may also be utilized by one or more applications executed by devices, such as the input devices 103, a wireless device 114, or a computing device 116. Any number of neuroprosthetics may be utilized as the input devices 103 or in their stead. In other embodiments the input devices 103 may represent more invasive probes, electrodes, surgical implants, or so forth that may be utilized for health or diagnostic reasons).

The processing system 100 may act as a communication pathway between a brain of a user (i.e., central nervous system), and one or more external computing devices. In one embodiment, the processing system 100 may digitally interface the user for the purpose of augmenting or repairing human cognition. For example, the EEG data 101 may be analyzed to address epilepsy, sleep disorders, encephalopathies, brain death, tumors, stroke, focal brain disorder, and so forth. Delta, Theta, Alpha, Beta, and Gamma waves of the EEG data 101 may represent key aspects of the EEG measurements utilized to determine the state-of-mind, mental stress, focus, or relaxation of users.

The EEG data 101 may be received directly from the input devices 103 or through one or more devices or networks. In one embodiment, the input devices 110 and 112 may communicate directly with the network 102 or a processing system that analyzes the EEG data 101. For example, any number of Bluetooth, Wi-Fi, cellular, or other radio frequency communications signals may be utilized to communicate the EEG data 101 and an analyzing device or separate processing system. In another embodiment, the input device 106 may communicate the EEG data 101 through a wired connection (e.g., packets, Ethernet, serial communications, parallel communications, etc.) to the wireless device 114 for subsequent communications. The wireless device 114 may communicate with the network 102 (e.g., routers, modems, cell towers, transceivers, etc.) utilizing a wireless network connection 118. The wireless network connection 118 may represent a Wi-Fi, Bluetooth, cellular, or other wireless connection, link, or signal. The input device 112 may be worn positioned substantially within the ear canal of the user.

In one embodiment, the processing system 100 may represent a client/server architecture in which the clients are represented by the input devices 103 and the servers are represented by the various devices and components of the network 102. In another embodiment, the wireless device 114, or the computing device 116 may perform the processing of the EEG data 101. In the illustrative embodiments, remotely networked devices, or local native devices may perform the processing of the EEG data 101. The brain wave analysis performed by the input devices 103 may be utilized to enhance performance or behavior of the user in a particular field-of-use or as a way of treating neurological and physical diseases, conditions, or issues. For example, music, audio, optical signals, electrical pulses of various frequencies may be utilized to treat a user in-situ, at a clinic, in a hospital, or so forth. In one embodiment, signal patterns may be utilized to affect the users.

The processing system 100 may analyze the different types of waves, variables, frequencies, and attributes of the EEG data 101. Some information regarding the various brain waves of the EEG data 101 are provided for purposes of understanding the analysis performed by the processing system 100 as well as a determined or estimated mental state of the user.

Delta Waves: Delta is the frequency range up to 4 Hz. Delta waves are often the highest in amplitude and the slowest waves. Delta waves are often observed in adults in slow wave sleep. Delta waves are also observed in babies. Delta was may occur focally with subcortical lesions and in general distribution with diffuse lesions, metabolic encephalopathy hydrocephalus or deep midline lesions. Delta waves usually occur most prominent frontally in adults (e.g. FIRDA—Frontal Intermittent Rhythmic Delta) and posteriorly in children (e.g. OIRDA—Occipital Intermittent Rhythmic Delta).

Theta Waves: Theta is the frequency range from 4 Hz to 7 Hz. Theta waves are often observed in young children. Theta waves may also be observed during drowsiness, meditation, or arousal in older children and adults. Excess theta waves for any given person's age represents abnormal activity. Theta waves may be seen as a disturbance in focal subcortical lesions and may be seen in generalized distribution in diffuse disorder, metabolic encephalopathy, deep midline disorders, or some instances of hydrocephalus. The range of with theta waves have often been associated with reports of relaxed, meditative, and creative states.

Alpha Waves: Alpha is the frequency range from 7 Hz to 14 Hz. Alpha waves are often referred to as the "posterior basic rhythm" (also called the "posterior dominant rhythm" or the "posterior alpha rhythm"), seen in the posterior regions of the head on both sides, higher in amplitude on the dominant side. Alpha waves may emerge when users close their eyes, with relaxation, and may attenuate with eye opening or mental exertion. The posterior basic rhythm is actually slower than 8 Hz in young children (therefore technically in the theta range). Sensorimotor rhythm is also known as mu rhythm. In addition to the posterior basic rhythm, there are other normal alpha rhythms such as the mu rhythm (alpha activity in the contralateral sensory and motor cortical areas) that emerges when the hands and arms are idle; and the "third rhythm" (alpha activity in the temporal or frontal lobes). Alpha may also be abnormal. For example, an EEG data 101 that has diffuse alpha occurring in coma and is not responsive to external stimuli is referred to as "alpha coma."

Beta Waves: Beta is the frequency range from 15 Hz to about 30 Hz. Beta waves are commonly seen on both sides in symmetrical distribution and are most evident frontally. Beta activity is closely linked to motor behavior and is generally attenuated during active movements. Low amplitude beta waves with multiple and varying frequencies may be often associated with active, busy or anxious thinking, and active concentration. Rhythmic beta with a dominant set of frequencies may be associated with various pathologies and drug effects, especially benzodiazepines. Beta waves may be absent or reduced in areas of the brain with cortical damage. Beta waves are the dominant rhythm in users/patients who are alert or anxious or who have their eyes open.

Gamma Waves: Gamma is the frequency ranges approximately 30 Hz to 100 Hz. Gamma rhythms may represent a binding of different populations of neurons together into a network for the purpose of carrying out a certain cognitive or motor functions.

Mu waves range from 8 Hz to 13 Hz, and partly overlaps with other frequencies. Mu waves reflect the synchronous firing of motor neurons in a rest state. Mu wave suppression is thought to reflect motor mirror neuron systems because when an action is observed, the pattern extinguishes, possibly because of the normal neuronal system and the mirror neuron system "go out of sync," and interfere with each other.

The processing system 100 may perform EEG analysis based on attributes of the users (not shown) of each of the input devices 103. For example, readings may vary based on the age of the user, sex, sleeping or mental state, ethnicity, physical attributes, and so forth.

Figure 2:
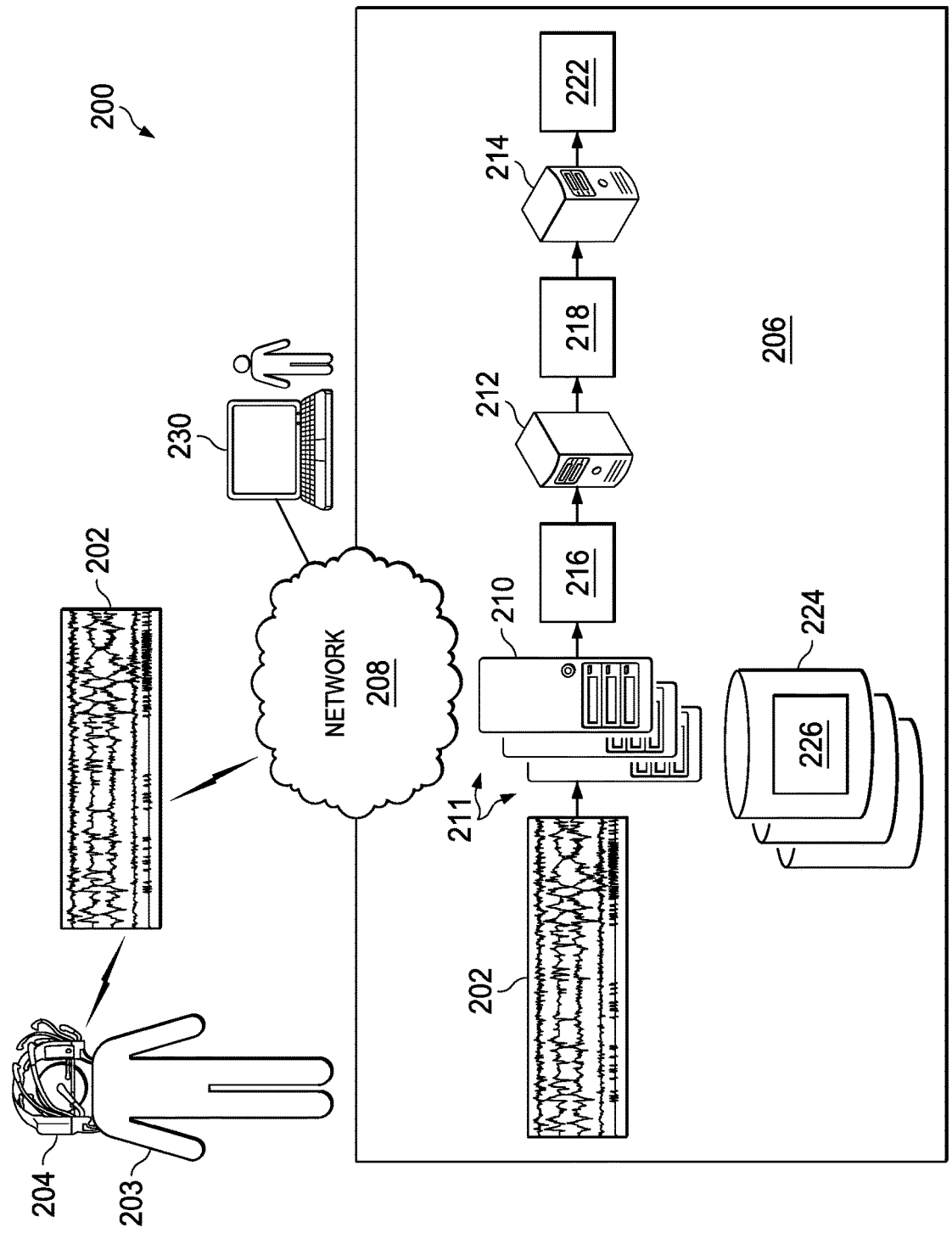
FIG. 2 is a pictorial representation of a server system for processing the EEG data of FIG. 1 in accordance with an illustrative embodiment.

FIG. 2 is a pictorial representation of another communication system 200 for processing the EEG data 202 in accordance with an illustrative embodiment. As shown, the EEG data 202 is captured from a user 203 by the input device 204. In one embodiment, the EEG data 202 is sent to a processing system 206 through a network 208. The network 208 may represent the Internet, a LAN, wireless networks, WANs, or any number or combination of other private and/or public networks. The EEG data 202 may be sent directly or indirectly to the processing system 206. Any number of communications connections or mediums (e.g., wireline, wireless, etc.) may be utilized to receive the EEG data 202. The EEG data 202 may be securely communicated. For example, the security may be at a level suitable for compliance with the Health Insurance Portability and Accountability Act of 1996 (HIPAA).

In one embodiment, the EEG data 202 is processed by one or more servers which may include a characterization server 210, an analysis server 212, and a trigger server 214 (jointly the "servers 211"). In other embodiments, the processing system 206 may represent a single server, cloud system, server farm, device, system, or equipment. The servers 211 may access one or more databases, such as database 224. The database 224 may include control data 226 utilized to further analyze the EEG data 202. The EEG data 202 may be processed and analyzed utilizing a number of customized or standard systems that may perform comparative, normative, and application specific analysis. The analysis performed by the processing system 206 may be performed automatically in response to the EEG data 202 being received. As a result, the EEG data 202 may be processed in real-time, near real-time, or at a later time based on saved or otherwise compiled EEG data 202.

The EEG data 202 may be processed by the characterization server 210 to generate the characterized data 216. The characterized data 216 may be processed by the analysis server 212 to generate the analyzed data 218. The analyzed data 220 may be processed by the trigger server 214 to generate the service response 222. Although FIG. 2 shows only the EEG data 202 received from the user 203 wearing the input device 204, the EEG data 202 may represent distinct data (e.g., discrete, streaming, etc.) received from any number of users and input devices, such as those shown in FIG. 1.

The characterizing server 210 performs characterizing and categorizing of the EEG data 202 to generate the characterized data 216. In one embodiment, the characterizing server 210 characterizes the EEG data 202 utilizing information associated with the user 203 utilizing the input device 204 to generate the EEG data 202. The characterizing server 210 may characterize the EEG data 202 to determine age, sex, body temperature, blood pressure, perspiration level, pulse rate, mental state (e.g., rested, tired, scared, alert, happy, anxious, excited, nervous, etc.), ethnicity, and other information associated with the user 203. The characterizing server 210 may determine any number of biometrics of the user 203 based on the input device 204, wearables, environmental sensors, or electronics associated with the user 203. For example, the EEG data 202 may be characterized based on the numeric age of the user 203 as expressed as a parameter in years, months, and/or days.

The characterizing server 210 may also categorize the EEG data 202. The categorization may determine a specified field-of-use applicable to the user 203. For example, the categorization may indicate whether the user 203 is participating in sports, health or medical treatments, truck driving, mining, or other activities. The EEG data 202 may also be categorized by the characterizing server 210 to indicate the mental or physical state of the user 203 at the time the EEG data 202 is created and captured by the input device 204. Categorization may be important because the state of mind and biofeedback indicated by the EEG data 202 may vary based on the activity and state of mind of the user 203. The state of the user 203 may indicate whether the user 203 is awake, sleeping, exercising, stressed, relaxed, resting, working, laughing, crying, seizing, or other state associated with a present activity, personality, or affliction of the user 203 at the time the EEG data 202 is captured by the input device 204. The characterizing server 210 may utilize the location, historical activities, designated activities, position, orientation, applications-in-use, or other information and data to categorize the activity being performed by the user 203.

The characterizing server 210 may also characterize and categorize the EEG data 202 based on the control data 226 or other information and data stored within the database 224. For example, the control data 202 may include activity, employment, medical, user profile, and other information associated with the user 203 or determined for other users.

The analysis server 212 may perform additional analysis and comparisons of the characterizing data 210. The analysis server 212 may determine whether the characterized data 216 conforms or does not conform with the control data 226. The analyzed data 218 may represent the results of further analyzing the characterized data 216. The control data 226 may represent benchmark data, standard values, historical data, expected results, patterns, normative ranges, thresholds, or so forth that may be specific to the user 203 or to users that are most similar to the user 203. The control data 226 may be generated utilizing any number of historical data sets associated with the user 203, similar users (e.g., subsets of users of similar age, ethnicity, health level, etc.), or large groups of users. For example, control data 226 that matches the characterized data features of the EEG data 202 as processed by the characterizing server 210 may be utilized for analysis.

The analyzed data 218 may be utilized by the trigger server 214 to generate the service response 222. The service response 222 may include a series of digital and executable commands, content, code instructions to other devices within the communication system 200, and specified stimuli. The service response 222 may be sent to the user 203 or third parties 230. The third parties 230 may represent any number of authorized users, administrators, caregivers, parents, coaches, officers-in-charge, devices, systems, or other individuals, groups, companies, or organizations. The third parties 230 may be set by the user 203 or an administrator. For example, the user 203 may specify individuals, such as parents, coaches, trainers, tracking systems, or medical professionals that are allowed to receive the queued data as well as the associated contact information or method (e.g., cell phone and number, IP address, text message and number, email and email address, phone call and phone number, etc.). In one embodiment, the user 203 may specify whether the data may be transmitted as saved, queued, or in real-time. In another embodiment, an administrator, such as a parent, guardian, coach, or medical professional, may specify the devices, individuals, businesses, or organizations included within the third parties 230 as well as the associated contact information. In one embodiment, the service response 222 may include data, control, command, software, or physical responses sent to the user 203, input device 204, or other devices, components, equipment, or users in the environment of the user 203.

At any time, the processing system 206 may send the raw EEG data 202, characterized data 216, analyzed data 218, service response, or data, information, or signals at any state of processing within the processing system 206, to compatible, excepting, or authorized systems represented by the third parties 230. As a result, the information and data captured, characterized and categorized, analyzed, and generated service responses may be checked, verified, authenticated, duplicated, or otherwise monitored.

The service response 222 may be generated based on conformance or nonconformance of the analyzed data 218, with expected results. The service response 222 may represent specified service responses for different fields-of-use. The service response 222 may include adaptive targeted content, computer code, or triggers that may be performed by the input device 204 or an associated wireless, computing, gaming, entertainment, or control device, system, or component. The service response 222 may also include any number of reports or alerts associated with the EEG data 202 of the user 203.

In one embodiment, the user 203 is a worker in the construction industry and the EEG data 202 applies to the user as she operates heavy machinery while wearing the input device 204. The EEG data 202 may be sent through a Wi-Fi network for local processing by the construction company or a construction consortium or to an external organization or body with sufficient processing power, such as the processing system 206 to perform the processing and analysis of the EEG data 202. In another embodiment, the EEG data 202 may be process by a specialized wireless device in communication with the input device 204. As a result, the EEG data 202 may be effectively and quickly processed at a construction site without the need for additional networks or processing systems.

In another embodiment, the EEG data 202 is characterized and categorized by the characterization server 210 to generate the characterized data 216. The EEG data 202 may be compared against the control data 226 of similar control subjects, such as females, within the construction industry, operating heavy machinery, within a selected age range, and ethnicity. The characterized data 216 may be further processed by the analysis server 212 to determine the fatigue level and mental state of the user 203 within the communication system 200. The analyzed data 218 is utilized by the trigger server 214 to generate the service response 222. The service response 222 may be utilized in an ongoing process to monitor the user 203. If a determination is made by the processing system 206 that the user is physically or mentally fatigued, access to the worksite, heavy machinery, or so forth may be limited automatically. For example, the user 203 may be required to take a 15-minute to 30-minute break. In other examples, specific thresholds regarding physical or mental state may automatically lock the user 203 out of critical systems for a preset time period (e.g., 30 minutes, 12 hours, etc.).

In another example, the service response 222 may include an alert that is sent to a supervisor or managerial staff indicating the conformance or nonconformance of the EEG data 202 with a desired result (i.e., ideal expected results from the control data 226). The supervisor may then make a decision regarding whether the user 203 may continue to operate the heavy machinery. The service response 222 may also be sent directly or indirectly to one or more systems or devices.

In another embodiment, the user is an inmate or patient in a corrections or treatment facility. The EEG data 202 may be captured by a source probe (e.g., input device 204). The EEG data 202 may be characterized and categorized by the characterization server 210. The EEG data 202 may be categorized as it relates to a 48-year-old Caucasian male in the corrections facility. The characterized data 216 may then be compared against the control data 226 to determine whether the aggression level and mental state of the user 203 indicates that he may be a danger to himself and/or others. The analyzed data 218 may be then communicated from the analysis serer 212 to the trigger server 214. In one embodiment, the service response 222 generated may limit the users access to specific portions of the facility as well as to other individuals within the facility (e.g., employees, other inmates or patients, etc.). The trigger server 214 may generate a trigger response that implements an action plan for the facility. In one embodiment, the trigger server 214 may automatically activate monitoring systems, such as a surveillance system, user biometrics, enhanced security, and other systems. In a home monitoring environment, the trigger response may activate a warning system to indicate that the user 203 is not allowed to leave his residence. The trigger response may also engage an audio/entertainment system as a way of calming the user 203 with specified music, entertainment, or other media. The service response 222 may represent any number of preemptive activities and actions that may help, protect, and calm the user 203.

In another embodiment, the user 203 may represent a soldier or contractor for the armed forces. The EEG data 202 may be analyzed to determine the mental readiness, concentration levels, calmness, fatigue levels, and mental state of the user 203. In one embodiment, the input device 204 may be built into a helmet, user monitor, heads-up display (HUD), communications headset, or other equipment, devices, or sub-system associated with the user 203. For example, the input device 204 may be connected to an aircraft, Humvee, tank battleship, marine vehicle, machinery, or other land, air, or water vehicles utilized as a tool or transport vessel by the user 203. The EEG data 202 may be utilized to determine whether the user 203 is ready and able to utilize the vehicle as well as the associated equipment, devices, features, and functions, and systems. The service response 222 may delivery fully processed data to compatible systems that may allow or deny the user 203 access to vehicles, systems, equipment, devices, scenarios, operations, jobs, tasks, and so forth as described herein. The service response 222 may automatically grant or deny access in real-time or may require approval from a third party (e.g., commander, administrator, supervisor, etc.) before granting or denying access. The process may be implemented for training, day-to-day activities, combat, or other operations and procedures the user 203 may participate in. For example, in response to determining the user 203 is under extreme duress, monitoring activities for the group associated with the user 203 may be implemented. In another example, weapons systems may be taken off-line in response to determining the user 203 is no longer in control of his emotions.

In one embodiment, the service response 222 may be compiled for a number of users and sent to a person-in-charge to make a decision, such as the ideal soldiers for an assignment, job, or task based on their current physical, mental, and emotional state as determined by EEG readings from a number of input devices. For example, conformance or nonconformance of the users' data (e.g., EEG data 202) with the control data 226 may be utilized to generate the analyzed data 218 and subsequently the service response 222. The service response 222 may implement display of applicable information to the user 203 as well as other users proximate or associated with the user 203. Any number of other actions may also be implemented.

In another embodiment, the communications system 200 may be applicable to the transportation industry. For example, the user 203 may represent a driver, pilot, captain, or operator of a vehicle or system, such as aircraft, busses, cruise ships, trucks, and other passenger, cargo, and mass transit vehicles and systems. The EEG data 202 processed by the processing system 206 may be similarly utilized to generate the service response 222 to control access to job sites, cockpits, control panels, command bridges, driver's seats, navigation systems, drive systems, or so forth. In one embodiment, the service response 222 may send an alert indicating that the user 203 needs to be relieved, actively engaged, or stimulated because of fatigue, intoxication, or mental readiness.

In other embodiments, the communications system 200 may be applicable to the physical therapy, pharmaceutical, and behavioral health industries. The EEG data 202 may be processed by the processing system 206 for the purposes of generating the service response 222 to perform diagnosis, real-time interventions, therapy, treatment, assessments, monitoring, prescribed medicine responses, effectiveness of treatment analysis, or other applications. For example, the types of brain waves present in the EEG data 202 may indicate the status of the user.

In other embodiments, the communication system 200 may be applicable to sports (e.g., professional, collegiate, recreational, personal, etc.) or human performance industries. The EEG data 202 may be processed by the processing system 206 for the purposes of determining calmness, mental distress, mental trauma, physical condition and so forth. The service response 222 may be generated to perform real-time analysis of sports performance, concussion analysis, implement commands, execute control systems, initiate or enhance performance and biometric monitoring, and other applications.

In one embodiment, the database 224 may store, queue, copy, or archive the EEG data 202 and other data within the processing system 206 as it is processed to generate the service response 222. The database 224 may store the service response 222 so that it may be searched, sorted, and accessed on-demand. For example, the EEG data 202 and the service responses 222 may be searched from any number of computing or communications devices with authorized access to the processing system 206 and the associated data. For example, the processing platform 206 may execute a database management system to access and control the raw and processed data.

Figure 3:
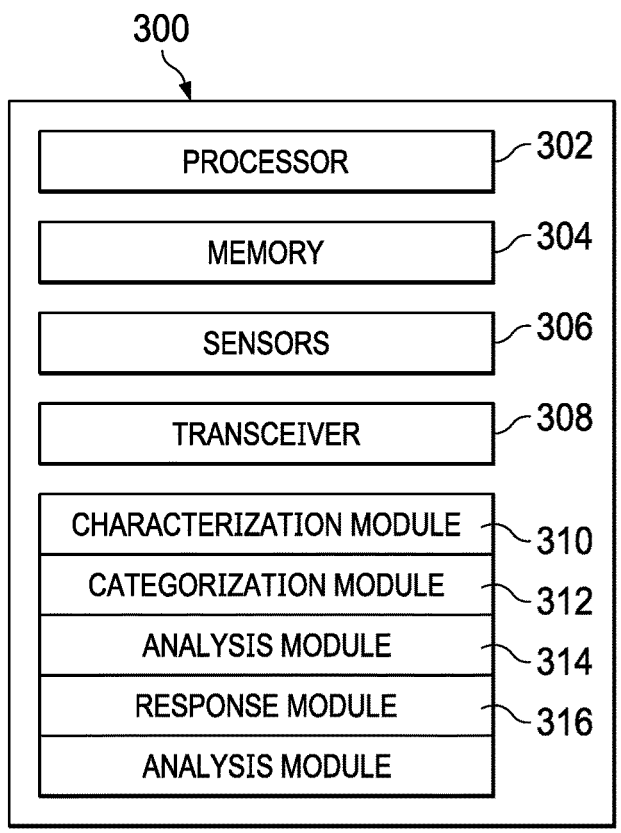
FIG. 3 is a block diagram of a processing system in accordance with an illustrative embodiment.

FIG. 3 is a block diagram of a processing system 300 in accordance with an illustrative embodiment. The processing system 300 is one embodiment of a computing or communications device configured to process EEG data received from any number of devices. For example, the processing system 300 may represent a server. The processing system 300 may process the EEG data locally, through a direct connection, or through one or more networks. In one embodiment, the processing system 300 may be integrated with an EEG reading device, such as a headset, virtual reality device, helmet, or so forth.

In one embodiment, the processing system 300 may include a processor, a memory, sensors 306, a transceiver 308, a characterization module 310, a categorization module 312, an analysis module 314, and a response module 316.

In one embodiment, the processor 302 is the logic that controls the operation and functionality of the processing system 300. The processor 302 may include circuitry, chips, and other digital logic. The processor 302 may also include programs, scripts, and instructions that may be implemented to operate the processor 302. The processor 302 may represent hardware, software, firmware, or any combination thereof. In one embodiment, the processor 302 may include one or more processors. The processor 302 may also represent an application specific integrated circuit (ASIC) or field programmable gate array (FPGA). The processor 302 may utilize sensor measurements, user input, user preferences and settings, conditions, factors, and environmental conditions to process the EEG data from the user. The components of the processing system 300 may function separately or together to process the EEG data. For example, processing may be divided between multiple devices (e.g., characterization server, analysis server, trigger server, web server, etc.) in communication with the processing system 300 to increase the speed of processing and to load balance any processes being performed.

In one embodiment, the processor 302 may perform any number of mathematical, signal analysis, and statistical analysis, processing, and computation to process and compare the EEG data against control data. The processor 302 may utilize time and other sensor measurements as causal forces to enhance mathematical functions, analysis, and processing utilized to perform the processes, steps, and determinations herein described.

The processor 302 is configured to perform all or a substantial portion of the processing needed for the illustrative embodiments. In one embodiment, the processor 302 may perform characterization, categorization, analysis (e.g., comparative analysis), response generation, and communications and alerts. In one embodiment, the processor 302 is a logic engine including circuitry or logic enabled to control execution of a set of instructions. The processor 302 may be one or more microprocessors, digital signal processors, application-specific integrated circuits (ASIC), central processing units, or other devices suitable for controlling an electronic device, such as the processing system 300, including one or more hardware and software elements, executing software, instructions, programs, and applications, converting and processing signals and information, and performing other related tasks.

The memory 304 is a hardware element, device, or recording media configured to store data or instructions for subsequent retrieval or access at a later time. The memory 304 may represent static or dynamic memory. The memory 304 may include a hard disk, random access memory, cache, removable media drive, mass storage, or configuration suitable as storage for data, instructions, and information. In one embodiment, the memory 304 and the processor 302 may be integrated. The memory 304 may use any type of volatile or non-volatile storage techniques and mediums. The memory 304 may store information related to a number of applicable users, processing system 300, input device, user-specific EEG data, historical EEG data, thresholds, associated alerts, indicators, and warnings, and so forth. In one embodiment, the memory 304 may store, display, or communicate instructions, programs, drivers, or an operating system for controlling interconnected systems, interfaces, EEG devices, or other systems, equipment, devices or components. The memory 304 may also store biometric readings or user input required for specified data, functions, or features, authentication settings and preferences, thresholds, conditions, signal or processing activity, historical information, proximity data, and so forth.

The transceiver 308 is a component comprising both a transmitter and receiver which may be combined and share common circuitry on a single housing. The transceiver 308 may communicate utilizing Bluetooth, Wi-Fi, ZigBee, Ant+, near field communications, wireless USB, infrared, mobile body area networks, ultra-wideband communications, cellular (e.g., 3G, 4G, 5G, PCS, GSM, etc.), infrared, or other suitable radio frequency standards, networks, protocols, or communications. For example, the transceiver 308 may coordinate communications and actions between the processing system 300 and a number of input devices utilizing Wi-Fi communications. The transceiver 316 may also be a hybrid transceiver that supports a number of different communications. For example, the transceiver 316 may communicate with a wireless EEG headset (not shown) utilizing Bluetooth communications and with a cloud network and remote parties utilizing Ethernet communications.

The sensors 306 may include EEG sensors, probes, or detectors for reading EEG signals or the currents, potentials, or phase changes associated with the neuroelectrical changes within the brain of the user. In other embodiments, the sensors 306 may also include inertial sensors, pulse oximeters, accelerometers, gyroscopes, impact/force detectors, thermometers, photo detectors, barometers, altimeters, global positioning systems, speedometers, miniature cameras, microphones (e.g., ear-bone, external, etc.), and other similar instruments for reading information, data, and other biometrics associated with the user or the environment of the user. The sensors 306 may also be utilized to determine the biometric, activity, location, and speed measurements of the user. In one embodiment, the sensors 306 may store data that may be shared with other components, users, and devices. The sensor data may also be utilized to perform automated actions, implement processes, or so forth. For example, the processing system 300 may generate responses to the EKG readings that may include wave forms (e.g., bianaural beats, monaural tones, isochronic tones, etc.) for trigging brain frequency changes. As a result, the processing system 300 may adjust the user's behavior, response, or reaction to various stimuli.

The processing system 300 may include characterization module 310, categorization module 312, analysis module 314, and response module 316. The various modules may represent hardware, software, firmware, or a combination thereof. The characterization module 310 may be utilized to perform characterization as herein described, including without limitation determining information associated with the user (e.g., age, sex, ethnicity, etc.), physical status (e.g., pulse, temperature, etc.), and mental/emotional status (e.g., calm, agitated, scared, excited, etc.). The characterization module 310 may receive feedback from the sensors 306 as well as input devices, such as EEG devices which may include user interfaces. Thus, the characterization module 310 may automatically determine categorization details or may receive data and information from the user, databases, communications systems, or other devices, systems, or parties.

The categorization module 312 may be utilized to determine categorization as herein described, including without limitation determining an activity associated with the user. The categorization module 312 may determine the activity based on the user's position, location, orientation, speed, calendar, altitude, activity level, or so forth. The characterization module 310 and the categorization module 312 may communicate with medical record databases, employment records, emergency databases, or so forth.

The analysis module 314 analyzes data that has been characterized and categorized. The analysis module 314 may store control data that may be compared against the incoming EEG data stream. The analysis module 314 may analyze the characterized and categorized data to determine compliance, noncompliance, or deviations with expected or desired EEG data. The control data may be specific to the user or may be generated based on other groups, groups of individuals, or so forth.

The response module 316 may utilize the analyzed data to determine a response based on the EEG data. The response module 316 may utilize the analyzed data to generate alerts, responses, dynamic feedback for the user, commands, sets of instructions, indicators, flags, or other responses. The communications from the response module 316 may be sent to the user, designated parties/devices, or any number of third parties.

In one embodiment, all or portions of the processing system may include non-transitory computer-readable media. The non-transitory computer-readable media may include all computer-readable media except for a transitory propagating signal within the processing system 300. For example, binaural beats data may be sent to the user to subliminally alter the brain waves of the user to a desired state or condition utilizing audio communicated to the user.

The components of the processing system 300 may be electrically connected utilizing any number of wires, contact points, leads, busses, wireless interfaces, or so forth. In addition, the processing system 300 may include any number of computing and communications components, devices or elements which may include busses, batteries, motherboards, circuits, chips, sensors, ports, interfaces (e.g., user, card, port, hardware, etc.), cards, converters, adapters, connections, transceivers, displays, antennas, and other similar components.

Figure 4:
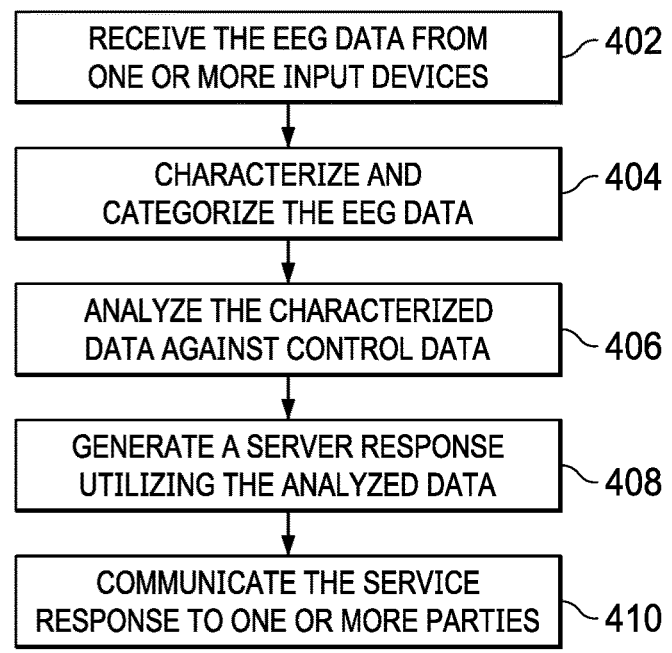
FIG. 4 is a flowchart of a process for processing EEG data in accordance with an illustrative embodiment.

FIG. 4 is a flowchart of a process for processing EEG data in accordance with an illustrative embodiment. The process of FIG. 4 may be implemented by one or more systems or devices, such as a server as is referenced herein. In one embodiment, the process of FIG. 4 may be implemented by a server and database configured to communicate with a number of EEG capture devices directly or indirectly. FIG. 4 may also be implemented by a series or group of servers (e.g., characterization and categorization, analysis, trigger, etc.) configured to receive EEG data from any number of sources. The process of FIG. 4 may alternatively be performed by a wireless device that receives the EEG data. The steps of FIG. 4 may be performed jointly, separately, or in any number of combinations of orders (e.g., sequentially, concurrently, simultaneously, etc.).

The process of FIG. 4 may begin by receiving EEG data from one or more input devices (step 402). As previously noted, the EEG data may be captured by any number of input/output devices, such as helmets, headsets, sunglasses, electronic headgear, virtual reality device, earpieces, probes, transponders, or so forth. The EEG data may be received for a single user or for multiple users utilizing the input devices. The server may be configured to process a single stream of EEG data or multiple streams of data simultaneously. The EEG data may be received directly by the server or through any number of intermediary devices or networks. In one embodiment, the EEG data may be packaged or packetized by the input devices for communication. The EEG data may also be encoded, encrypted, or otherwise formatted for efficient communication as well as security. In other embodiments, the EEG data may be sent in a raw format as read by the input devices (e.g., raw analogic or digital EEG readings, etc.).

Next, the server characterizes and categorizes the EEG data (step 404). Characterization may include age, sex, pulse rate, ethnicity, and other factors that may affect the EEG readings performed by the input devices. Characterization may also include determining the state of mind or mental state of the user. Categorization may include determining an activity the user is engaged in, such as football player, train driver, truck driver, airplane pilot, crane operator, surgeon, and any number of activities, industries, or professions the user is engaged in. In one embodiment, one or more external databases or devices may be utilized to determine information and data that is utilized to perform the characterization and categorization. For example, the server may access a database, application, or interface of employee information, medical records, user entered information, and other applicable information that is automatically determined, captured over time, or user generated.

Next, the server analyzes the characterized data against control data (step 406). During step 406, the characterized and categorized data is compared against control data that may include standardized, baseline, normative, threshold, performance based, or other data and information. The server may determine whether the EEG data conforms or does not conform with the control data during step 406 to generate analyzed data. In one embodiment, the server may determine whether changes to the environment, equipment, parameters, circumstances, or environment that affect the user may need to be made. For example, the user, administrator, or other party may want the EEG data for the user to be as close as possible to the EEG data.

Next, the server generates service response utilizing the analyzed data (step 408). The service response may represent a response to the user's EEG data as analyzed by the server. The service response may include any number of active or passive responses. For example, a coach, administrator, supervisor, parent, or other interested party may provide input or feedback (e.g., in-person, audibly, visually, tactilely, etc.) to the user in response to the EEG data. The feedback may be sent through the input devices, utilizing associated devices (e.g., vehicle systems, weapon systems, cell phones, computing devices, etc.), or utilizing devices in the user's environment. The service response may be utilized control one or more actions, provide feedback, pre-emptively act (e.g., rotate soldiers to prevent post-traumatic stress, change drivers, provide additional stimulus to calm the user, provide positive feedback to help a scared user, etc.), provide precursor information.

Next, the server communicates the service response to one or more parties (step 410). The service response may be communicated to individuals, groups, organizations, systems, devices, equipment, components or so forth. For example, the service response may be communicated to the user, the input device, or any number of other third parties as processed EEG data, warnings, alerts, recommendations, or so forth. In one embodiment, the service response may include digital content, computer code, or one or more trigger commands.

In one embodiment, the service response may include binaural beats. Neurons within the brain generate electric currents and the synchronous action of the neurons may represent macroscopic oscillations which may be monitored by the EEG data capture for the user. Such oscillations may be characterized by frequency, amplitude, and phase. Neural tissue within the brain may generate oscillatory activity driven by mechanisms within individual neurons as well as their interactions. Audio signals may be generated by the input devices wherein the jointly processed (e.g., by the inferior colliculus of the midbrain and the superior olivary complex of the brainstem) to generate electrical impulses of the neural pathways up the midbrain to the thalamus, auditory cortex, and other cortical regions of the brain. Sounds, music, or other signals may be generated to best precipitate different changes in the neural oscillations and correlating EEG readings of the user to alter the user's cognitive and emotional state. This processed may also be referred to as neuronal entrainment or brain wave entrainment. In one embodiment, binaural beats, monaural tones, and isochronic tones may be utilized as a triggered response for brain wave entrainment. Each different type of response may have advantages and disadvantages for specific brain waves (e.g., Beta, Alpha, Theta, Delta, etc.). In one embodiment, isochronic tones may be utilized to achieve a desired response in the user.

The illustrative embodiments provide for systems, devices, and methods for processing brain wave data into a systematic and homogenous format for processing. As a result, the brain wave data, such as EEG data, may be more effectively processed. In addition, responses may be more effectively generated including audio inputs, electrical brain wave stimulation, visual stimulation The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 5:
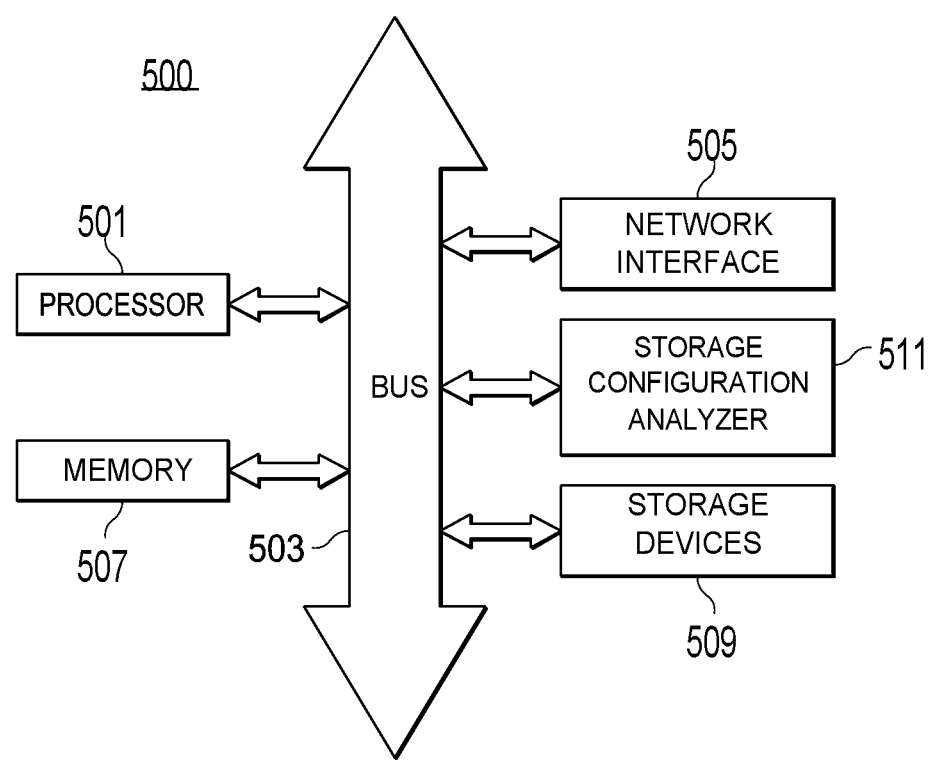
FIG. 5 is a pictorial representation of a computing system in accordance with an illustrative embodiment.

FIG. 5 depicts a computing system 500 in accordance with an illustrative embodiment. For example, the computing system 500 may represent a server or processing system, such as the processing system 300 of FIG. 3. The computing system 500 may be utilized to process EEG data by performing characterization, categorization, analysis, response generation, and so forth. The computing system 500 includes a processor unit 501 (possibly including multiple processors, multiple cores, multiple nodes, and/or implementing multi-threading, etc.). The computing system includes memory 507. The memory 507 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 503 (e.g., PCI, ISA, PCI-Express, HyperTransport®, InfiniBand®, NuBus, etc.), a network interface 505 (e.g., an ATM interface, an Ethernet interface, a Frame Relay interface, SONET interface, wireless interface, etc.), a storage configuration analyzer 511, and a storage device(s) 509 (e.g., optical storage, magnetic storage, etc.). The system memory 507 embodies functionality to implement embodiments described above. The system memory 507 may include one or more functionalities that facilitate retrieval of the audio information associated with an identifier. Code may be implemented in any of the other devices of the computing system 500. Any one of these functionalities may be partially (or entirely) implemented in hardware and/or on the processing unit 501. For example, the functionality may be implemented with an application specific integrated circuit, in logic implemented in the processing unit 501, in a co-processor on a peripheral device or card, etc. Further, realizations may include fewer or additional components not illustrated in FIG. 5 (e.g., video cards, audio cards, additional network interfaces, peripheral devices, etc.). The processor unit 501, the storage device(s) 509, and the network interface 505 are coupled to the bus 503. Although illustrated as being coupled to the bus 503, the memory 507 may be coupled to the processor unit 501.

The present invention is not to be limited to the particular embodiments described herein. In particular, the present invention contemplates numerous variations in the type of ways in which embodiments of the invention may be applied to [Insert high-level or more detailed description of the invention]. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method of processing electroencephalography (EEG) data, the method comprising:
   reading the EEG data from a user utilizing one or more EEG input devices worn by the user, the one or more EEG input devices sense EEG data and biometrics of the plurality of users;
   communicating the EEG data and the biometrics to one or more processing devices;
   characterizing the EEG data utilizing the one or more processing devices to generate characterized data;
   categorizing the characterized data utilizing the one or more processing devices to determine a user activity and status of the user associated with the EEG data;
   analyzing the characterized data to generate analyzed data, wherein during analysis the characterized data is compared against control data corresponding to the characterized data and associated with the user and stored by the one or more processing devices; and
   generating a service response for one or more systems in communication with the one or more EEG devices to control ignition, locks, and operations of the one or more systems in response to the analyzed data and the biometrics.

2. The method of claim 1, wherein the one or more input devices include at least a helmet or a headset worn by the user.

3. The method of claim 1, wherein the one or more processing devices are integrated with the one or more EEG input devices.

4. The method of claim 1, wherein the service response includes command codes for the one or more processing devices.

5. The method of claim 1, wherein the service response includes stimuli applied to the user utilizing at least the one or more EEG input devices.

6. The method of claim 1, wherein the control data includes baseline data and historical data for only the user.

7. The method of claim 1, wherein the generating a service response further comprises:
sending one or more alerts to designated users.

8. The method of claim 1, further comprising:
communicating the service response to the one or more systems through a transceiver.

9. The method of claim 1, wherein the EEG data is communicated wirelessly to the one or more processing devices utilizing a transceiver.

10. The method of claim 1, further comprising:
providing a stimulus through the one or more EEG input devices as part of the service response.

11. A processing system for EEG data comprising:
a plurality of input devices sensing EEG data from a plurality of users, the plurality of input devices are worn by the plurality of users and capture the EEG data from the user;
a plurality of sensors within each of the plurality of input devices capture measurements including biometric data of each of the plurality of users, orientation, location, and speed of the plurality of users;
a processor receives the EEG data and the biometric data of each of the plurality of users, characterizes the EEG data received from the plurality of users to generate characterized data, categorizes the characterized data utilizing the one or more processing devices to determine a user activity and status of each of the plurality of users associated with the EEG data, analyzes the characterized data to generate analyzed data, wherein during analysis the characterized data is compared against control data corresponding to the characterized data and associated with only the user stored by the one or more processing devices, and generates a service response for one or more systems in communication with the one or more EEG devices to control one or more of ignition, locks, and operations of the one or more systems in response to the analyzed data and the biometric data.

12. The processing system of claim 10, wherein each of the plurality of input devices and the plurality of sensors and the processor are included in a helmet or headset.

13. The processing system of claim 10, further comprising:
a transceiver configured to communicate the service response to the one or more systems.

14. The processing system of claim 10, wherein the service response includes authorized commands for the one or more processing devices.

15. A processing system comprising:
one or more EEG input devices worn on a head of a user and capturing EEG data and biometrics directly utilizing a plurality of sensors,
a memory storing a set of instructions, the EEG data, and the biometrics;
a processor executing the set of instructions, wherein the instructions are executed by the processor to:
characterize the EEG data utilizing the one or more processing devices to generate characterized data, categorize the characterized data utilizing the one or more processing devices to determine a user activity and status of the user associated with the EEG data, analyze the characterized data to generate analyzed data, wherein the characterized data is compared against control data for the user corresponding to the characterized data and stored by the one or more processing devices, and generate a service response for one or more systems in communication with the one or more EEG devices to control start up, locks, and operations of the one or more systems in response to the analyzed data and the biometrics.

16. The processing system of claim 15, wherein the set of instructions are further executed to determine an activity, orientation, location, and speed of the user utilizing the EEG data and the biometrics.

17. The processing system of claim 15, wherein the service response includes authorized commands for the one or more processing devices.

18. The processing system of claim 15, wherein the plurality of input devices, the plurality of sensors, the processor, and the memory are included in a helmet or headset.

19. The processing system of claim 15, wherein the service response is generated based on an activity of the user.

20. The processing system of claim 15, wherein the service response is one of a plurality of predetermined service responses including at least requiring the user to take a break, activating an alert, granting access to the one or more systems, providing a stimulus to the user, and providing instructions to the user, and wherein the control data is associated with baseline data and historical data for only the user.

* * * * *